US012713507B2

(12) United States Patent
Broersma et al.

(10) Patent No.: US 12,713,507 B2
(45) Date of Patent: Aug. 18, 2026

(54) LIGHT GENERATING SYSTEM

(71) Applicant: SIGNIFY HOLDING B.V., Eindhoven (NL)

(72) Inventors: Remy Cyrille Broersma, Eindhoven (NL); Marcel Petrus Lucassen, Landsmeer (NL); Bianca Maria Irma Van Der Zande, Heeze (NL); Tobias Borra, Rijswijk (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 26 days.

(21) Appl. No.: 19/099,151

(22) PCT Filed: Jul. 20, 2023

(86) PCT No.: PCT/EP2023/070158
§ 371 (c)(1),
(2) Date: Jan. 28, 2025

(87) PCT Pub. No.: WO2024/022943
PCT Pub. Date: Feb. 1, 2024

(65) Prior Publication Data

US 2026/0046990 A1 Feb. 12, 2026

(30) Foreign Application Priority Data

Jul. 28, 2022 (EP) .................................... 22187511

(51) Int. Cl.
*H05B 47/16* (2020.01)
*A61N 5/06* (2006.01)
(Continued)

(52) U.S. Cl.
CPC ........... *H05B 47/16* (2020.01); *A61N 5/0613* (2013.01); *H05B 47/11* (2020.01); *H05B 47/115* (2020.01);
(Continued)

(58) Field of Classification Search
CPC ...... H05B 47/16; H05B 47/11; H05B 47/115; H05B 47/155; H05B 47/17; H05B 47/19;
(Continued)

(56) References Cited

U.S. PATENT DOCUMENTS 11,785,694 B2 * 10/2023 Hamm .................. G06F 3/0482 315/294
12,081,358 B2 * 9/2024 Bard ................... H04L 12/2816
(Continued)

FOREIGN PATENT DOCUMENTS

EP 4561693 B1 * 12/2025 .......... F21V 33/0064
WO 2015077734 A1 5/2015
(Continued)

*Primary Examiner* — Adam D Houston

(57) ABSTRACT

The invention provides a light generating system (1000) comprising (a) first light generating device (110) and (b) a control system (300), wherein: the first light generating device (110) is configured to generate first device light (111), wherein the first device light (111) comprises light having one or more wavelengths in a first wavelength range of 280-320 nm, wherein the first wavelength range comprises a lower subrange from λ11 to λ12 and a higher subrange from λ21 to λ22, wherein 280 nm≤λ11<λ12≤λ21<λ22≤320 nm, and wherein λ12 and λ21 are selected from the wavelength range of 290-315 nm, wherein a wavelength dependent radiant flux of the first device light (111) is controllable: the light generating system (1000) is configured to generate system light (1001) comprising at least part of the first device light (111); the control system (300) is configured to control the wavelength dependent radiant flux of the first device light (111) as a function of time, wherein the light generating system (1000) is configured to provide the first device light (111) at a first time t1, at a second time t2, and at a third time t3; wherein the second time t2 is temporally arranged after the first time t1, and the third time t3 is temporally arranged after the second time t2; and wherein
(Continued)

the first time t1, the second time t2, and the third time t3 are temporally arranged in a single day; wherein relative to a total radiant flux in the first wavelength range the radiant flux of the first device light (111) in the lower subrange is relatively lower at the first time t1 than at the second time t2, and wherein relative to the total radiant flux in the first wavelength range the radiant flux of the first device light (111) in the higher subrange is relatively higher at the first time t1 than at the second time t2; and/or wherein relative to the total radiant flux in the first wavelength range the radiant flux of the first device light (111) in the lower subrange is relatively higher at the second time t2 than at the third time t3, and wherein relative to the total radiant flux in the first wavelength range the radiant flux of the first device light (111) in the higher subrange is relatively lower at the second time t2 than at the third time t3.

15 Claims, 4 Drawing Sheets

(51) Int. Cl.
*H05B 47/11* (2020.01)
*H05B 47/115* (2020.01)
*H05B 47/155* (2020.01)
*H05B 47/17* (2020.01)
*H05B 47/19* (2020.01)

(52) U.S. Cl.
CPC .......... *H05B 47/155* (2020.01); *H05B 47/17* (2020.01); *H05B 47/19* (2020.01); *A61N 2005/0628* (2013.01); *A61N 2005/0659* (2013.01); *A61N 2005/0661* (2013.01); *A61N 2005/0662* (2013.01)

(58) Field of Classification Search
CPC .......... A61N 5/0613; A61N 2005/0628; A61N 2005/0659; A61N 2005/0661; A61N 2005/0662; A61N 2005/0626; A61N 2005/0636; F21V 33/0064; F21Y 2113/30; A61B 2017/00176
See application file for complete search history.

(56) References Cited

U.S. PATENT DOCUMENTS

| | | | | |
|---|---|---|---|---|
| 12,267,931 | B2 * | 4/2025 | Jarboe | A61N 5/0618 |
| 12,465,784 | B2 * | 11/2025 | Gerstenmeier | A61N 5/0614 |
| 2004/0232359 | A1 * | 11/2004 | Fiset | A61N 5/0614 250/504 R |
| 2014/0207215 | A1 * | 7/2014 | Fiset | A61N 5/0614 607/94 |
| 2015/0292143 | A1 | 10/2015 | Wang et al. | |
| 2017/0374722 | A1 * | 12/2017 | Beiner | H05B 47/18 |
| 2018/0318599 | A1 | 11/2018 | Van Bommel et al. | |
| 2019/0268990 | A1 * | 8/2019 | Janik | H05B 47/11 |
| 2020/0376292 | A1 | 12/2020 | Moffat et al. | |
| 2021/0275826 | A1 * | 9/2021 | Kawarai | A61D 1/00 |
| 2022/0016437 | A1 | 1/2022 | Jarausch | |
| 2024/0021381 | A1 * | 1/2024 | Dimberg | G08C 17/02 |
| 2025/0089146 | A1 * | 3/2025 | Donners | H05B 45/20 |

FOREIGN PATENT DOCUMENTS

| | | | | |
|---|---|---|---|---|
| WO | WO-2019118773 | A1 * | 6/2019 | A61B 5/445 |
| WO | WO-2020169383 | A1 * | 8/2020 | H05B 47/10 |
| WO | 2021148580 | A1 | 7/2021 | |
| WO | WO-2023280665 | A1 * | 1/2023 | A61L 9/013 |
| WO | WO-2023006471 | A1 * | 2/2023 | H05B 47/17 |
| WO | WO-2024022943 | A1 * | 2/2024 | A61N 5/0613 |
| WO | WO-2024160652 | A1 * | 8/2024 | H05B 47/17 |
| WO | WO-2026027419 | A1 * | 2/2026 | A61M 21/00 |

* cited by examiner

LIGHT GENERATING SYSTEM

CROSS-REFERENCE TO PRIOR APPLICATIONS

This application is the U.S. National Phase application under 35 U.S.C. § 371 of International Application No. PCT/EP2023/070158, filed on Jul. 20, 2023, which claims the benefit of European Patent application Ser. No. 22187511.5, filed on Jul. 28, 2022. These applications are hereby incorporated by reference herein.

FIELD OF THE INVENTION

The invention relates to a light generating system. The invention further relates to a lighting device.

BACKGROUND OF THE INVENTION

Light generating devices are known in the art. For instance, US2020376292A1 describes dynamic dosing systems for phototherapy and associated devices, systems, and methods. In some embodiments, a dynamic dosing phototherapy system can include a self-service phototherapy kiosk ("SPK") configured to emit UV radiation, a user interface communicatively coupled to the SPK, and a dynamic dosing system communicatively coupled to the user interface and the SPK. The dynamic dosing system can determine initial, user-specific parameters specific to define a first individual phototherapy protocol, and then determine adjustments to the initial parameters and the first individual phototherapy protocol based on user inputs related to erythema response to a previous phototherapy treatment session. The SPK can deliver UV radiation to a user in accordance with the first individual phototherapy protocol and/or an adjusted, second phototherapy protocol that takes into account the user's erythema response.

SUMMARY OF THE INVENTION

Natural daylight contains a wide variety of UV wavelengths, and the UV spectrum may change considerably upon changing solar zenith angles (SZA). For instance, the UV spectrum may change substantially as a function of zenith solar angle. At a latitude of 45° North, at low angles (sun high in the sky; e.g., at 6°), UV rays of ~ 290 nm may be substantially more abundant in the sun spectrum than at higher solar angles (low standing sun; e.g., at 86°). In particular, in the morning, in the evening and in wintertime, wavelengths above about 297 nm may be substantially more prevalent than below about 297 nm.

The human body may contain a variety of photo receptors. Photo-receptors may (at least partially) regulate biological processes in the human body as a function of wavelengths of light they are exposed to. For instance, the production of vitamin D in the human body may depend on absorption of UVB by the skin. The vitamin D hormone, which may be important for health and for instance for bone strength, may be the end result of a cascade of photochemical reactions occurring in the skin. In particular, the reaction constant of the different photochemical reactions in the vitamin D synthesis pathway may be wavelength-dependent.

Throughout human history, humans have primarily been exposed to natural sunlight (or "daylight"), and the photoreceptors may have developed accordingly to appropriately regulate biological processes as a function of the exposure to sunlight, the spectrum of which may vary substantially throughout the day. Nowadays, many people may be predominantly exposed to artificial lighting, which may typically provide light with a single static spectrum throughout the day. The exposure to such a static spectrum may result in a relatively static activation of the photoreceptors, which may substantially impact biological processes, such as the synthesis of vitamin D. In particular, as compared to sunlight, artificial light may provide relatively little vitamin D synthesis.

Vitamin D deficiency may nowadays be rather prevalent, especially at high latitudes. Generally, a vitamin D deficiency may be addressed through food supplements.

Hence, it is an aspect of the invention to provide an alternative light generating system, which preferably further at least partly obviates one or more of above-described drawbacks. The present invention may have as object to overcome or ameliorate at least one of the disadvantages of the prior art, or to provide a useful alternative.

According to a first aspect, the invention provides a light generating system ("system") comprising (a) first light generating device and (b) a control system. In embodiments, the first light generating device may be configured to generate first device light, especially wherein the first device light comprises light having one or more wavelengths in a first wavelength range of 280-320 nm. In particular, the first wavelength range may comprise a lower subrange from $\lambda_{11}$ to $\lambda_{12}$ and a higher subrange from $\lambda_{21}$ to $\lambda_{22}$, especially wherein 280 nm$\leq\lambda_{11}<\lambda_{12}\leq\lambda_{21}<\lambda_{22}\leq$320 nm, such as wherein $\lambda_{12}$ and $\lambda_{21}$ are selected from the wavelength range of 290-315 nm. In further embodiments, a wavelength dependent radiant flux of the first device light is controllable. The light generating system may especially be configured to generate system light comprising (at least part of) the first device light. The control system may be configured to control the wavelength dependent radiant flux of the first device light as a function of time, especially wherein the light generating system may be configured to provide the first device light at a first time t1, at a second time t2, and at a third time t3. The second time t2 is temporally arranged after the first time t1, and the third time t3 is temporally arranged after the second time t2. The first time t1, the second time t2, and the third time t3 are temporally arranged in a single day Thus: t1<t2<t3. In particular, in embodiments, relative to a total radiant flux in the first wavelength range the radiant flux of the first device light in the lower subrange may be relatively lower at the first time t1 than at the second time t2, and wherein relative to the total radiant flux in the first wavelength range the radiant flux of the first device light in the higher subrange may be relatively higher at the first time t1 than at the second time t2. In further embodiments, relative to the total radiant flux in the first wavelength range the radiant flux of the first device light in the lower subrange is relatively higher at the second time t2 than at the third time t3, and wherein relative to the total radiant flux in the first wavelength range the radiant flux of the first device light in the higher subrange is relatively lower at the second time t2 than at the third time t3.

Hence, in specific embodiments, the invention may provide a light generating system comprising (a) first light generating device and (b) a control system, wherein: the first light generating device is configured to generate first device light, wherein the first device light comprises light having one or more wavelengths in a first wavelength range of 280-320 nm, wherein the first wavelength range comprises a lower subrange from $\lambda_{11}$ to $\lambda_{12}$ and a higher subrange from $\lambda_{21}$ to $\lambda_{22}$, wherein 280 nm$\leq\lambda_{11}<\lambda_{12}\leq\lambda_{21}<\lambda_{22}\leq$320 nm, and wherein $\lambda_{12}$ and $\lambda_{21}$ are selected from the wavelength range of 290-315 nm, wherein a wavelength dependent radiant flux of the first device light is controllable; the light generating system is configured to generate system light comprising at least part of the first device light; the control system is configured to control the wavelength dependent radiant flux of the first device light as a function of time, wherein the light generating system is configured to provide the first device light at a first time t1, at a second time t2, and at a third time t3; wherein relative to a total radiant flux in the first wavelength range the radiant flux of the first device light in the lower subrange is relatively lower at the first time t1 than at the second time t2, and wherein relative to the total radiant flux in the first wavelength range the radiant flux of the first device light in the higher subrange is relatively higher at the first time t1 than at the second time t2; and/or wherein relative to the total radiant flux in the first wavelength range the radiant flux of the first device light in the lower subrange is relatively higher at the second time t2 than at the third time t3, and wherein relative to the total radiant flux in the first wavelength range the radiant flux of the first device light in the higher subrange is relatively lower at the second time t2 than at the third time t3.

In aspects, alternatively phrased, the light generating system is configured to provide the first device light at two or more of: a first time t1, a second time t2, and a third time t3. In aspects, the control system is configured to control the wavelength dependent radiant flux of the first device light in the lower subrange and in the higher subrange dynamically as a function of time.

With such a light generating system, the (relative) abundance of different wavelengths of light may be varied over the day, in order to dynamically stimulate photoreceptors, such as by mimicking natural sunlight. In particular, the light generating system may at the second time t2 provide first device light with a higher proportion of radiant flux in the lower subrange (relative to the total radiant flux in the first wavelength range) than at the first time t1 and/or at the third time t3. Hence, the second time t2 may, for instance, correspond to noon, when the sun is at a low zenith angle, whereas first time t1 and third time t3 may, for instance, correspond to morning and evening, when the sun is at a high zenith angle.

The invention may herein primarily be discussed in relation to vitamin D synthesis, which synthesis may generally be known to depend on the exposure to UV radiation. It will be clear to the person skilled in the art, however, that a variety of other processes in the human body may involve or be regulated by photoreceptors, such as processes controlling the circadian rhythm, and that the light generating system of the invention may also be beneficially applied in the context of regulating such processes.

As mentioned above, vitamin D synthesis may involve a cascade of biochemical reactions which may be differentially affected by different wavelengths of light. In particular, the photoconversion of vitamin D relevant derivatives may strongly depend on the wavelength. Since the spectral content of the solar radiation varies during the day due to the changing solar angle, especially in the UVB wavelength range (itself), the equilibrium between the different derivatives will also vary during the day. For instance, the quantum yields may be essentially wavelength-independent for the conversions of lumisterol (Lumi) to previtamin D3 (Pre), of provitamin D3 (7-dehydrocholesterol, Pro) to Pre, and of tachysterol (Tachy) to Pre, but may rise at longer wavelengths (from about 300+ nm) for Pre to Pro and for Pre to Lumi, and may fall at longer wavelengths (from about 300+ nm) for Pre to Tachy. Hence, a changing spectrum may change the photogeneration of the derivatives lumisterol and tachysterol from previtamin D substantially. A situation that may essentially not occur with a static light spectrum and only intensity variation. Norval et al., "Is the action spectrum for the UV-induced production of previtamin D3 in human skin correct?", Photochemical & Photobiological Sciences, 2010, which is hereby herein incorporated by reference, calculated based on extinction coefficients determined in ethanol that there are distinct differences in the obtained mixture of previtamin D, provitamin D and lumisterol and tachysterol concentrations upon varying the UV irradiance wavelength. In particular, at wavelengths<290 nm the main metabolic direction may be tachysterol. At wavelengths of about 280 to about 305 nm, the conversion may be directed towards previtamin D at the expense of tachysterol, while at longer UVB wavelengths a shift towards lumisterol at the expense of previtamin D and tachysterol may take place. This may implicate that upon changing solar spectra during the day, the direction towards synthesis of previtamin D and tachysterol may evolutionary be preferred during low solar zenith angles (midday), while the synthesis might shift towards a reduced previtamin D and increased lumisterol at higher solar zenith angles (morning, late afternoon, and winter). Although in the past lumisterol and tachysterol may have been thought to be inactive components of the vitamin D synthesis, it appears that these vitamin D derivatives also have biological activity, even possibly distinct from vitamin D.

Experimental studies using lasers and filtered arc lamps may show a similar result. In particular, the Tachysterol levels may be highest at short UV wavelengths, such as at around 248 nm, and may be lowest at the higher wavelengths, such as at about 308 nm. Previtamin D levels may be highest at an intermediate wavelength, such as at about 290 nm, and may stabilize upon prolonged exposure, while at shorter and longer wavelengths previtamin D levels may decay at longer exposure times. Based on the kinetic calculations and measurements from Terenetskaya, "Limitations of the photostationary approximation in the photochemistry of provitamin D: The ambiguous role of the irreversible degradation channel", Theoretical and Experimental Chemistry, 2008, which is hereby herein incorporated by reference, the accumulation of previtamin D may be highest between 266 and 300 nm. The high accumulation of previtamin D may hamper further conversion because of the establishment of a kinetic equilibrium. For further conversions, previtamin D may first need to be converted into vitamin D, lumisterol or tachysterol.

The light generating system of the invention may especially provide a dynamic spectral shift, such as for copying the effect that sunlight gives on the vitamin D synthesis metabolism. By having a dynamic UVB spectral solution, it may provide the vitamin D rich diversity of the vitamin D synthesis as does natural sunlight, distinct from artificial static solutions and supplements. In particular, the light generating system of the invention may facilitate (i) providing a variety of different vitamin D compounds throughout the day similar to natural sunlight, (ii) deplete the skin from previtamin D, to enhance (due to shifting reaction equilibrium kinetics) conversion from provitamin D to previtamin D upon subsequent exposures as natural sunlight will do in the morning and late afternoon; and provide the right vitamin D metabolites at the right time of the day (circadian dynamic metabolite shift). The present invention is a clear improvement, for example, over lighting systems providing a single static spectrum comprising UVB.

Hence, the invention may provide a light generating system. The light generating system may comprise a first light generating device. The term "a first light generating device" may also refer to a plurality of first light generating devices. In particular, the first light generating device may be configured to generate first device light, and the light generating system may be configured to provide system light, wherein the system light comprises (at least part of) the first device light.

The first light generating device may be configured to generate first device light; especially wherein the first device light comprises light having one or more wavelengths in a first wavelength range. In embodiments, the first wavelength range may comprise the range of 270-330 nm, such as the range of 280-320 nm. The first wavelength range may especially comprise the UVB wavelength range.

In embodiments, the first wavelength range may comprise a lower subrange from $\lambda_{11}$ to $\lambda_{12}$ and a higher subrange from $\lambda_{21}$ to $\lambda_{22}$, especially wherein 280 nm$\leq\lambda_{11}<\lambda_{12}\leq\lambda_{21}<\lambda_{22}<$320 nm. In further embodiments, $\lambda_{11}$ may be selected from the range of 280-300 nm, such as from the range of 280-295 nm, especially from the range of 280-290 nm. In further embodiments, $\lambda_{12}$ and $\lambda_{21}$ may be selected from the wavelength range of 285-315 nm, such as from the range of 290-315 nm, especially from the range of 290-310 nm. In further embodiments, $\lambda_{22}$ may be selected from the range of 300-320 nm, such as from the range of 305-320 nm, especially from the range of 310-320 nm. In particular, in embodiments, $\lambda_{11}$ may be selected from the range of 280-290 nm, $\lambda_{12}$ and $\lambda_{21}$ may be selected from the range of 295-305 nm, and $\lambda_{22}$ may be selected from the range of 310-315 nm.

The first wavelength range may especially consist of the first subrange and the second subrange. For instance, in specific embodiments, the first wavelength range may comprise the range of 280-300 nm, and the second wavelength range may comprise the range of 300-320 nm. However, in further embodiments, the first wavelength range may also comprise wavelengths outside of the first subrange and the second subrange.

In embodiments, a wavelength dependent radiant flux of the first device light may be controllable, i.e. the first light generating device may be controlled to provide first device light with different spectra. In particular, the spectrum of the first device light may be controlled by controlling the first light generating device. For instance, in embodiments, radiant fluxes at different wavelengths may be controlled (at least partially) independently of one another.

The light generating system may further comprise a control system, especially wherein the control system is configured to control the wavelength dependent radiant flux of the first device light. Hence, the control system may be configured to control the light spectrum of the first device light.

In embodiments, the control system may be configured, especially in an operational mode, to control the wavelength dependent radiant flux of the first device light as a function of time, especially wherein the light generating system is configured to provide the first device light at one or more of a first time t1, a second time t2, and a third time t3, especially at least at the first time t1 and at the second time t2, or especially at least at the second time t2 and at the third time t3.

As described above, the second time t2 may especially correspond to noon, at which the sun is at a low zenith angle, whereas the first time t1 and the second time t3 may correspond to morning and/or evening, at which times the sun is at a high zenith angle. For instance, in embodiments, the first time t1 may be selected from a first day time range or from a third day time range, especially from a first day time range. Similarly, the second time t2 may be selected from a second day time range. Yet similarly, the third time t3 may be selected from the third day time range or from a first day time range, especially from the third day time range.

In further embodiments, the first day time range may comprise the range of from 04:00 to 11:00 hours, such as the range of from 04:00 to 10:00 hours, especially the range of 04:00 to 09:00 hours.

In further embodiments, the second day time range may comprise the range of 9:00 to 16:00 hours, such as the range of 10:00 to 15:00 hours, especially the range of 11:00 to 14:00 hours.

In further embodiments, the third day time range may comprise the range of 14:00 to 20:00 hours, such as the range of 15:00 to 20:00 hours, especially the range of 16:00 to 20:00 hours.

Especially, in embodiments when selecting the first day time range, the second day time range and the third day time range, they do not mutually overlap in time.

It will be clear to the person skilled in the art that the spectrum of natural sunlight received at the surface of the earth is not directly dependent on the time of day, but may rather be dependent on the solar zenith angle (and on weather conditions), and that the solar spectrum provided at a specific site at a specific time may depend, for instance, on the geographical location of that specific site within a time zone, as well as on whether it is summer time or winter time (if applicable) at that specific site. In particular, the spectrum of natural sunlight at the specific site may depend more directly on the time relative to solar noon, i.e., the time relative to the moment when the sun reaches the highest point in the sky for the specific site.

Hence, in embodiments, the second day time range may comprise the range of TN−3−TN+3 hours, wherein TN is solar noon, especially wherein TN is solar noon at the site where the light generating system is located. For instance, if solar noon is at 14:00 and the second day time range comprises the range of TN−3−TN+3 hours, then the second day time range may comprise the range of 11:00-17:00 hours. In further embodiments, the second time t2 may be selected from the range of TN−2.5−TN+2.5 hours, such as from the range of TN−2−TN+2 hours, especially from the range of TN−1.5−TN+1.5 hours.

Similarly, in embodiments, the first day time range may comprise the range of 4:00 to TN−1.5 hours, such as 4:00 to TN−2 hours, especially 4:00 to TN−2.5 hours, such as 4:00 to TN−3 hours.

In further embodiments, the third day time range may comprise the range of TN+1.5-20:00 hours, such as the range of TN+2-20:00 hours, especially the range of TN+2.5-20:00 hours, such as the range of TN+3-20:00 hours.

Hence, as mentioned, the first time t1, the second time t2, and the third time t3 may all be temporally arranged in a single day. In particular, especially within the single day, the second time t2 may be temporally arranged after the first time t1, and the third time t3 may be temporally arranged after the second time t2.

In particular, all times referred to herein are in the 24-hour format. Hence, "11:00" corresponds to 11:00 AM in the 12-hour format, and 11:00 PM in the 12-hour format will be referred to herein as "23:00".

In embodiments, the control system may, especially in the operational mode, be configured to control the wavelength dependent radiant flux of the first device light such that one or more, especially both, applies of: (a) relative to a total radiant flux in the first wavelength range the radiant flux of the first device light in the lower subrange is relatively lower at the first time t1 than at the second time t2, and (b) relative to the total radiant flux in the first wavelength range the radiant flux of the first device light in the higher subrange is relatively higher at the first time t1 than at the second time t2.

In further embodiments, the control system may, especially in the operational mode, be configured to control the wavelength dependent radiant flux of the first device light such that one or more, especially both, applies of: (a) relative to the total radiant flux in the first wavelength range the radiant flux of the first device light in the lower subrange is relatively higher at the second time t2 than at the third time t3, and (b) relative to the total radiant flux in the first wavelength range the radiant flux of the first device light in the higher subrange is relatively lower at the second time t2 than at the third time t3.

In further embodiments, the control system may, especially in the operational mode, be configured to control the wavelength dependent radiant flux of the first device light such that (a) relative to a total radiant flux in the first wavelength range the radiant flux of the first device light in the lower subrange is relatively lower at the first time t1 than at the second time t2, (b) relative to the total radiant flux in the first wavelength range the radiant flux of the first device light in the higher subrange is relatively higher at the first time t1 than at the second time t2, (c) relative to the total radiant flux in the first wavelength range the radiant flux of the first device light in the lower subrange is relatively higher at the second time t2 than at the third time t3, and (d) relative to the total radiant flux in the first wavelength range the radiant flux of the first device light in the higher subrange is relatively lower at the second time t2 than at the third time t3.

In embodiments, the control system may be configured, especially in the operational mode, to control the first device light such that between t1 and t2 and/or between t2 and t3 there is a gradual change, especially a continuous change, from $Lt1/Ft1$ to $Lt2/Ft2$, or especially from Rt1 to Rt2 (see below). In particular, in embodiments, the gradual change in the lower subrange may be at a rate of at least (about) $0.1*(Lt2-Lt1)$ per hour. Similarly, in embodiments, the gradual change in the higher subrange may be at a rate of at least (about) $0.1*(Ht2-Ht1)$ per hour.

Hence, some time may pass between t1 and t2 wherein the radiant fluxes of the first device light gradually change. For instance, in embodiments, t1 and t2 may be at least 0.5 hours apart, such as at least 1 hour apart, especially at least 2 hours apart. Alternatively, in embodiments, the control system may be configured, especially in the operational mode, to control the first device light such that between t1 and t2 there is a stepwise change, especially an instantaneous change from $Lt1/Ft1$ to $Lt2/Ft2$, or especially from Rt1 to Rt2 (see below). For instance, in such embodiments, t1 may be temporally arranged within 5 minutes from t2, such as within 1 minute, especially within 10 seconds. Similarly, in such embodiments, t3 may be temporally arranged within 5 minutes from t2, such as within 1 minute, especially within 10 seconds.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The system, or apparatus, or device may execute an action in a "mode" or "operation mode" or "mode of operation" or "operational mode". The term "operational mode may also be indicated as "controlling mode". Likewise, in a method an action or stage, or step may be executed in a "mode" or "operation mode" or "mode of operation" or "operational mode". This does not exclude that the system, or apparatus, or device may also be adapted for providing another controlling mode, or a plurality of other controlling modes. Likewise, this may not exclude that before executing the mode and/or after executing the mode one or more other modes may be executed.

As described above, the first light generating device may be configured to provide first device light with different levels of wavelength-dependent radiant fluxes over time. In embodiments, the first light generating device may be configured to provide first device light with in the first wavelength range (i) a first full radiant flux Ft1 at first time t1 (or "time t1") and (ii) a second full radiant flux Ft2 at second time t2 (or "time t2"), i.e., Ft1 and Ft2 may be radiant fluxes in the first wavelength range at time t1 and time t2, respectively. Similarly, in embodiments, the first light generating device may be configured to provide first device light within the lower subrange (i) a first lower radiant flux Lt1 at first time t1 and (ii) a second lower radiant flux Lt2 at second time t2 (or "time t2"), i.e., Lt1 and Lt2 are radiant fluxes of the lower subrange at time t1 and time t2, respectively. In further embodiments, the first light generating device may be configured to provide first device light within the higher subrange (i) a first higher radiant flux Ht1 at first time t1 and (ii) a second higher radiant flux Ht2 at second time t2 (or "time t2"), i.e., Ht1 and Ht2 are radiant fluxes of the higher subrange at time t1 and time t2, respectively.

In such embodiments, one or more of the following may apply: (a) $Lt2/Ft2 \geq 1.01*Lt1/Ft1$, and (b) $Ht2/Ft2 \leq 0.99*Ht1/Ft1$.

In further embodiments, $Lt2/Ft2 \geq 1.01*Lt1/Ft1$, such as $Lt2/Ft2 \geq 1.05*Lt1/Ft1$, especially $Lt2/Ft2 \geq 1.10*Lt1/Ft1$. In further embodiments, $Lt2/Ft2 \geq 1.2*Lt1/Ft1$, such as $Lt2/Ft2 \geq 1.5*Lt1/Ft1$, especially $Lt2/Ft2 \geq 2*Lt1/Ft1$. In further embodiments, $Lt2/Ft2 \geq 5*Lt1/Ft1$, such as $Lt2/Ft2 \geq 10*Lt1/Ft1$, especially $Lt2/Ft2 \geq 20*Lt1/Ft1$.

In further embodiments, $Ht2/Ft2 \leq 0.99*Ht1/Ft1$, such as $Ht2/Ft2 \leq 0.98*Ht1/Ft1$, especially $Ht2/Ft2 \leq 0.97*Ht1/Ft1$, such as $Ht2/Ft2 \leq 0.95*Ht1/Ft1$, especially such as $Ht2/Ft2 \leq 0.9*Ht1/Ft1$.

In particular, towards solar noon, such as from t1 to t2, the radiant flux of natural sunlight may increase throughout the first wavelength range. However, the increase may be relatively larger at shorter wavelengths than at longer wavelengths (also see FIG. 1B).

Hence, compared to the full radiant flux in the first wavelength range, the relative radiant flux in the higher wavelength range may decrease from t1 to t2 ($Ht1/Ft1>Ht2/Ft2$), while in the lower subrange the relative radiant flux from t1 to t2 may substantially increase ($LHt1/Ft1<Lt2/Ft2$).

For instance, in embodiments, one or more, especially both, of the following may apply: (a) $Lt2/Ft2 \geq 2*Lt1/Ft1$ and (b) $Ht2/Ft2 \leq 0.95*Ht1/Ft1$.

Similarly, in embodiments, Ft3, Ht3 and Lt3 are radiant fluxes in the first wavelength range, in the higher wavelength range, and in the lower subrange at time t3 respectively. In further embodiments, $Lt2/Ft2>2*Lt3/Ft3$. In yet further embodiments, $Ht2/Ft2<0.99*Ht3/Ft3$.

In further embodiments, $Lt2/Ft2 \geq 1.01*Lt3/Ft3$, such as $Lt2/Ft2 \geq 1.05*Lt3/Ft3$, especially $Lt2/Ft2 \geq 1.10*Lt3/Ft3$. In further embodiments, $Lt2/Ft2 \geq 1.2*Lt3/Ft3$, such as $Lt2/Ft2 \geq 1.5*Lt3/Ft3$, especially $Lt2/Ft2 \geq 2*Lt3/Ft3$. In further embodiments, $Lt2/Ft2 \geq 5*Lt3/Ft3$, such as $Lt2/Ft2 \geq 10*Lt3/Ft3$, especially $Lt2/Ft2 \geq 20*Lt3/Ft3$.

In further embodiments, $Ht2/Ft2 \leq 0.99*Ht3/Ft3$, such as $Ht2/Ft2 \leq 0.98*Ht3/Ft3$, especially $Ht2/Ft2 \leq 0.97*Ht3/Ft3$, such as $Ht2/Ft2 \leq 0.95*Ht3/Ft3$, especially such as $Ht2/Ft2 \leq 0.9*Ht3/Ft3$.

Similarly, in embodiments, at a first time t1 the light generating system may provide first device light having a first radiant flux ratio Rt1 of the radiant flux in the higher subrange relative to the radiant flux in the lower subrange; and at a second time t2 the light generating system provides first device light having a second radiant flux ratio Rt2 of the radiant flux in the higher subrange relative to the radiant flux in the lower subrange; wherein $Rt1/Rt2 \geq 2$. In particular, in embodiments, the following may apply: $Rt1=Ht1/Lt1$, $Rt2=Ht2/Lt2$, and $Rt1/Rt2>1$, such as $\geq 1.5$, especially $\geq 2$, such as $\geq 5$. In further embodiments, the following may apply: $Rt3=Ht3/Lt3$, $Rt2=Ht2/Lt2$, and $Rt3/Rt2>1$, such as $\geq 1.5$, especially $\geq 2$, such as $\geq 5$.

In further embodiments, $2 \leq Rt1/Rt2 \leq 2000$, especially $3 \leq Rt1/Rt2 \leq 1000$, such as $5 \leq Rt1/Rt2 \leq 500$. Similarly, in further embodiments, $2 \leq Rt3/Rt2 \leq 2000$, especially $3 \leq Rt3/Rt2 \leq 1000$, such as $5 \leq Rt3/Rt2 \leq 500$.

As described above, the invention may facilitate providing system light (to a person) mimicking sunlight, which may beneficially stimulate biological processes. In particular, in embodiments, the light generating system, especially the control system, may be configured to provide the first device light according to (average) daily patterns, such as in view of the latitude and the time of the year. For instance, in embodiments, the control system may be configured to control the first device light in dependence of one or more of a (current) season (of the year) and a latitude of the light generating system, i.e., the latitude corresponding to the geographical location of the light generating system.

In further embodiments, the light generating system may comprise or be functionally coupled to a sensor, wherein the control system is configured to control the first light generating device, especially the first device light, in dependence of the sensor. Especially, the sensor may be configured to sense a parameter and to provide a related parameter signal to the control signal, wherein the control system is configured to control the first device light in dependence on the related parameter signal. For instance, in embodiments, the sensor may comprise one or more of a presence sensor, such as a motion sensor, and a daylight sensor.

In embodiments, the sensor may comprise a presence sensor, such as a motion sensor, configured to detect whether a space is occupied and to provide a presence-related signal to the control system, wherein the control system is configured to control the first light generating device based on the presence-related signal. For instance, in embodiments, the light generating system may be configured to provide system light to a space, and the presence sensor is configured to detect whether the space is occupied, and the control system may be configured to control the first light generating device to only provide the first device light if, based on the presence-related signal, the space is occupied.

In particular, in embodiments, the sensor may comprise a daylight sensor, especially wherein the daylight sensor is configured to sense (natural) daylight, and to provide a related daylight signal to the control system.

The term "daylight-related signal" may herein refer to a signal that is related to the detected daylight. In particular, the daylight-related signal may comprise raw and/or processed data related to the (detected) daylight, such as raw and/or processed data related to radiant fluxes in the daylight, especially in the first wavelength range.

In further embodiments, the control system may be configured to control the first light generating device to provide first device light mimicking the (detected) (essentially) concurrent sunlight based on the daylight-related signal, especially wherein the control system is configured to control the first light generating device to provide first device light mimicking the radiant fluxes in the concurrent sunlight based on the daylight-related signal.

Although the invention may herein primarily be described in the context of mimicking spectral changes in natural sunlight in a daily pattern, it will be clear to the person skilled in the art that the invention is not limited to such embodiments. For instance, given that different wavelengths of light may steer biological processes in different directions (via the photoreceptors, it may be advantageous to provide larger relative differences than those naturally occurring as a function of the solar zenith angle, such as by (essentially) temporally separating the presence of different wavelengths in the first device light. Thereby, the light generating system of the invention may facilitate (essentially) independently controlling different biological processes by providing the relevant wavelengths (for these processes) at different times.

For instance, in embodiments, one or more, especially all, of the following may apply: $Lt1/Ft1 \leq 0.1$; $Lt2/Ft2 \geq 0.9$; and $Lt3/Ft3 \leq 0.1$, such as at least $Lt1/Ft1<0.1$ and $Lt2/Ft2 \geq 0.9$. In such embodiments, at the first time (and at the third time) there may be a relatively low abundance of radiant flux in the lower subrange relative to the total radiant flux in the first wavelength range, whereas at the second time t2 the radiant flux in the lower subrange may represent the vast majority of the total radiant flux in the first wavelength range.

In further embodiments, $Lt1/Ft1 \leq 0.2$, such as $Lt1/Ft1 \leq 0.1$, especially $Lt1/Ft1 \leq 0.01$, such as $Lt1/Ft1 \leq 0.001$, including 0. In further embodiments, $Lt2/Ft2 \geq 0.5$, especially $Lt2/Ft2 \geq 0.75$, such as $Lt2/Ft2 \geq 0.9$, such as $Lt2/Ft2 \geq 0.95$, including 1. In further embodiments, $Lt3/Ft3 \leq 0.2$, such as $Lt3/Ft3 \leq 0.1$, especially $Lt3/Ft3 \leq 0.01$, such as $Lt3/Ft3 \leq 0.001$, including 0.

As described above, in natural daylight, the relative change in radiant flux between (early) morning and solar noon may be larger for shorter wavelengths than for longer wavelengths in the first wavelength range. The change for shorter wavelengths may thus occur relatively faster. Similarly, in embodiments, during a change period tc a time dependent relative change of the wavelength dependent radiant flux of the first device light in the lower subrange may be larger than in the higher subrange.

In particular, in embodiments, the control system may be configured to provide the gradual change (see above) during the change period tc. In further embodiments, t1 and t2 may be arranged in the change period tc. In further embodiments, the change period tc may have a duration selected from the range of 0.5-10 hours, especially from the range of 1-8 hours, such as from the range of 2-4 hours.

In further embodiments, CL may be $|Lt1-Lt2|/(0.5*(Lt1+Lt2))$, and CH may be $|Ht1-Ht2|/(0.5*(Ht1+Ht2))$, especially wherein $CL \geq CH$, such as $CL \geq 1.5*CH$, especially $CL \geq 2*CH$, such as $CL \geq 3*CH$.

Similarly to change period tc during which the relative radiant fluxes (in the first wavelength range) in the first device light may change, the light generating system may further be configured to provide a holding period th during which the relative radiant fluxes may remain essentially constant. In further embodiments, during a holding period th a radiant flux Lh of the first device light in the lower subrange $\lambda_{11}$-$\lambda_{12}$ and a radiant flux Hh of the first device light in the higher subrange $\lambda_{21}$-$\lambda_{22}$ are maintained essentially constant, such as wherein Lh and Hh each vary at most 5% during the holding period th, such as at most 3%, especially at most 1%. Especially, the holding period th may be selected from the second day time range. In further embodiments, the holding period th may have a duration of at least 1 hour, such as of at least 2 hours, especially at least 3 hours. In further embodiments, the light generating system may be configured to provide first device light with an (essentially) constant spectral composition during the holding period th.

In embodiments, the first light generating device may be configured to generate first device light having a first spectral power of which at least 85% is in the first wavelength range, especially at least 90%, such as at least 95%, including 100%. In further embodiments, the first wavelength range may comprise n first wavelength range parts, especially n first wavelength range parts of (approximately) equal lengths. In such embodiments, the first device light integrated over the change period tc may include a radiant flux in k of these first wavelength range parts, especially wherein n is selected from the range of 2-8, such as from the range of 3-7, especially from the range of 4-6, and especially wherein $2 \leq k \leq n$, such as $3 \leq k \leq n$, especially $4 \leq k \leq n$.

As will be clear to the person skilled in the art, overexposure to UV radiation may be undesirable, for instance in view of potential adverse health effects. Hence, the irradiance of the light generating device may be selected in view of health and/or safety, such as in view of national and international guidelines.

In embodiments, the first light generating device may be configured to generate first device light having an irradiance, especially an actinic weighted irradiance, in the first wavelength range at 1 m distance from the first light generating device selected from the range of <3 $mW/m^2$, especially ≤1 $mW/m^2$.

The term "actinic weighted irradiance" as used herein corresponds to the term as defined in standard IEC 62471, chapter 4, which is hereby herein incorporated by reference and which is known to the person skilled in the art.

As the light generating system of the invention is directed to the provision of system light to persons, the light generating system may beneficially also provide visible light. For instance, a person may be more likely to consistently turn on the lights if they also provide visible light, given that the absence of visible light is obvious, whereas the absence of UVB may not be perceivable. Furthermore, light sources providing visible light may tend to be appropriately arranged to illuminate a space, which may provide a suitable arranged for the first light generating devices as well.

Hence, in embodiments, the light generating system may further comprise a second light generating device, especially wherein the second light generating device is configured to generate second device light having one or more wavelengths in the visible wavelength range. In particular, in an operational mode of the system the system light may comprise one or more of (i) (at least part of) the first device light and (ii) (at least part of) the second device light, especially (at least part of) the first device light and (at least part of) the second device light.

In particular, in embodiments, the second light generating device may be configured to generate white second device light, especially wherein a correlated color temperature of the second device light is controllable, and especially wherein the control system is configured to control the correlated color temperature of the second device light as function of time. In particular, it may be beneficial for a user of the light generating system, such as the occupant of a room the light generating system is configured to illuminate, to have a visual cue that the light generating system is active and/or working. Generally, people may relate UV to a violet or blue hue. Hence, the light generating system may, for instance, be configured to provide warmer light (i.e., having a higher CCT) at the second time t2 as compared to the first time t1 and/or the third time t3.

In further embodiments, the second light generating device may be configured to provide infrared (IR) radiation, such as near IR radiation, especially in the range of 750-3000 nm. In particular, NIR may be involved in restauration/aging of cells and hence may be beneficial in case UV is provided. The NIR can be applied prior, simultaneous or after the UV exposure. Hence, in embodiments, the system light may concurrently comprise the first device light and the second device light, or may provide the first device light and the second device light with a temporal separation.

The light generating system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, digital projection, or LCD backlighting. The light generating system (or luminaire) may be part of or may be applied in e.g. optical communication systems or disinfection systems.

The light generating system, especially the first light generating device, or especially the second light generating device, may comprise a light source. The (first/second) device light may in embodiments comprise one or more of light source light and converted light source light (such as luminescent material light).

The term "white light", and similar terms, herein, is known to the person skilled in the art. It may especially relate to light having a correlated color temperature (CCT) between about 1800 K and 20000 K, such as between 2000 and 20000 K, especially 2700-20000 K, for general lighting especially in the range of about 2000-7000 K, such as in the range of 2700 K and 6500 K. In embodiments, e.g. for backlighting purposes, or for other purposes, the correlated color temperature (CCT) may especially be in the range of about 7000 K and 20000 K. Yet further, in embodiments the correlated color temperature (CCT) is especially within about 15 SDCM (standard deviation of color matching) from the BBL (black body locus), especially within about 10 SDCM from the BBL, even more especially within about 5 SDCM from the BBL.

In specific embodiments, the correlated color temperature (CCT) may be selected from the range of 6000-12000 K, like selected from the range of 7000-12000 K, like at least 8000 K. Yet further, in embodiments the correlated color temperature (CCT) may be selected from the range of 6000-12000 K, like selected from the range of 7000-12000 K, in combination with a CRI of at least 70.

The terms "visible", "visible light" or "visible emission" and similar terms refer to light having one or more wavelengths in the range of about 380-780 nm. Herein, UV may especially refer to a wavelength selected from the range of 190-380 nm, such as 200-380 nm.

The terms "light" and "radiation" are herein interchangeably used, unless clear from the context that the term "light" only refers to visible light. The terms "light" and "radiation" may thus refer to UV radiation, visible light, and IR radiation. In specific embodiments, especially for lighting applications, the terms "light" and "radiation" refer to (at least) visible light.

The term IR radiation may in specific embodiments refer to near IR radiation (NIR). Therefore, herein also the term "(N) IR" is applied, to refer to in general IR, and in specific embodiments to NIR.

The terms "violet light" or "violet emission" especially relates to light having a wavelength in the range of about 380-440 nm. The terms "blue light" or "blue emission" especially relates to light having a wavelength in the range of about 440-495 nm (including some violet and cyan hues). The phrase "light having one or more wavelengths in a wavelength range" and similar phrases may especially indicate that the indicated light (or radiation) has a spectral power distribution with at least intensity or intensities at these one or more wavelengths in the indicate wavelength range. For instance, a blue emitting solid state light source will have a spectral power distribution with intensities at one or more wavelengths in the 440-495 nm wavelength range.

The control system may also be configured to receive and execute instructions from a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, Thread, WIFI, LiFi, ZigBee, BLE or WiMAX, or another wireless technology.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

In a further aspect, the invention may provide a lighting device selected from the group of a lamp, a luminaire, a projector device, a disinfection device, a photochemical reactor, a phototherapy lighting device, and an optical wireless communication device comprising the light generating system according to any one of the preceding claims, especially a lighting device selected from the group comprising a lamp, a luminaire, and a phototherapy lighting device.

Hence, the invention may also provide a lamp or a luminaire comprising the light generating system as defined herein. The luminaire may further comprise a housing, optical elements, louvres, etc, etc. The lamp or luminaire may further comprise a housing enclosing the light generating system. The lamp or luminaire may comprise a light window in the housing or a housing opening, through which the system light may escape from the housing. In yet a further aspect, the invention also provides a projection device comprising the light generating system as defined herein. Especially, a projection device or "projector" or "image projector" may be an optical device that projects an image (or moving images) onto a surface, such as e.g. a projection screen. The projection device may include one or more light generating systems such as described herein. Hence, in an aspect the invention also provides a light generating device selected from the group of a lamp, a luminaire, a projector device, a disinfection device, a photochemical reactor, and an optical wireless communication device, comprising the light generating system as defined herein. The light generating device may comprise a housing or a carrier, configured to house or support, one or more elements of the light generating system.

Instead of the terms "lighting device" or "lighting system", and similar terms, also the terms "light generating device" or "light generating system", (and similar terms), may be applied. A lighting device or a lighting system may be configured to generate device light (or "lighting device light") or system light ("or lighting system light"). As indicated above, the terms light and radiation may interchangeably be used.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
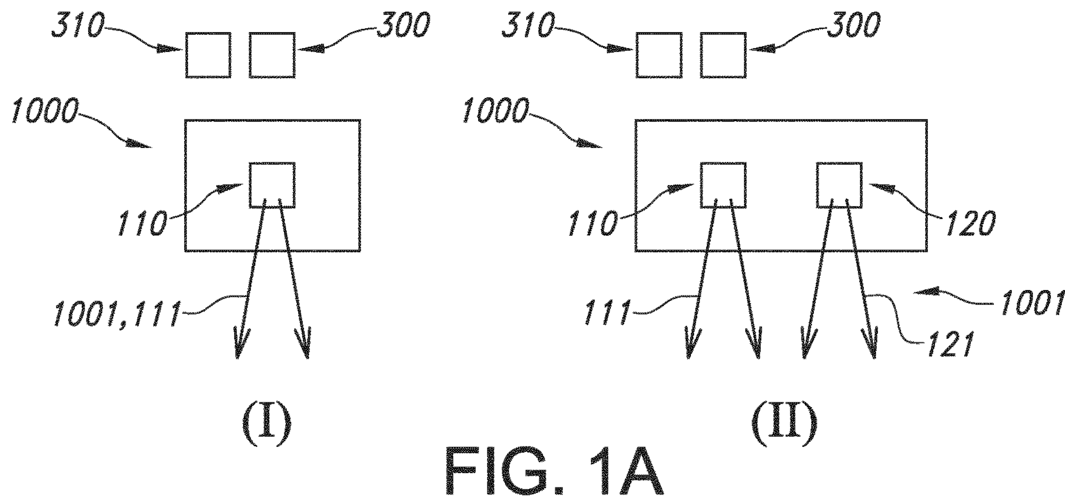
FIG. 1A schematically depicts embodiments of the light generating system.

FIG. 1 schematically depicts embodiments (I) and (II) of a light generating system 1000 comprising a first light generating device 110 and a control system 300. In the depicted embodiment, the first light generating device 110 is configured to generate first device light 111. In the depicted embodiment, the light generating system 1000 is configured to generate system light 1001 comprising at least part of the first device light 111. Especially, the first device light 111 may comprise light having one or more wavelengths in a first wavelength range of 280-320 nm. In particular, in embodiments, the first wavelength range may comprise a lower subrange from $\lambda_{11}$ to $\lambda_{12}$ and a higher subrange from $\lambda_{21}$ to $\lambda_{22}$, especially wherein 280 nm$\leq\lambda_{11}<\lambda_{12}\leq\lambda_{21}<\lambda_{22}\leq$320 nm, and especially wherein $\lambda_{12}$ and $\lambda_{21}$ are selected from the wavelength range of 290-315 nm. In further embodiments, a wavelength dependent radiant flux of the first device light 111 is controllable, especially wherein the control system 300 is configured to control the wavelength dependent radiant flux of the first device light 111 as a function of time. In particular, in embodiments, the light generating system 1000 may be configured to provide the first device light 111 at a first time t1 and at a second time t2, especially at the first time t1, the second time t2, and at the third time t3. In embodiments, relative to a total radiant flux in the first wavelength range the radiant flux of the first device light 111 in the lower subrange may be relatively lower at the first time t1 than at the second time t2, and relative to the total radiant flux in the first wavelength range the radiant flux of the first device light 111 in the higher subrange is relatively higher at the first time t1 than at the second time t2. In further embodiments, relative to the total radiant flux in the first wavelength range the radiant flux of the first device light 111 in the lower subrange is relatively higher at the second time t2 than at the third time t3, and relative to the total radiant flux in the first wavelength range the radiant flux of the first device light 111 in the higher subrange is relatively lower at the second time t2 than at the third time t3.

In embodiments, the first light generating device 110 may be configured to generate first device light 111 having an (actinic weighted) irradiance in the first wavelength range at 1 m distance from the first light generating device 110 (or from the light generating system 1000) selected from the range of ≤3 mW/m$^2$, especially ≤1 mW/m$^2$.

In the depicted embodiment, the light generating system 1000 may further comprise or be functionally coupled to a sensor 310. In particular, the sensor 310 may be configured to sense a parameter, such as a daylight spectrum, and provide a parameter-related signal to the control system 300, especially wherein the control system 300 is configured to control the first light generating device 110 based on the parameter-related signal.

For instance, in embodiments, the control system 300 may be configured to control the first device light 111 in dependence of a sensor 310, wherein the sensor 310 comprises a daylight sensor. In further embodiments, the sensor 310 may comprise a presence sensor or motion sensor.

In further embodiments, the control system 300 may be configured to control the first device light 111 in dependence of one or more of a (current) season (of the year) and a latitude of the light generating system 1000.

In the depicted embodiment (II), the light generating system 1000 further comprises a second light generating device 120, especially wherein the second light generating device 120 is configured to generate second device light 121 having one or more wavelengths in the visible wavelength range. In further embodiments, in an operational mode of the system 1000, the system light 1001 may comprise one or more of (i) at least part of the first device light 111 and (ii) at least part of the second device light 121, especially at least part of the first device light 111 and at least part of the second device light 121.

In particular, in embodiments, the second light generating device 120 may be configured to generate white second device light 121, wherein a correlated color temperature of the second device light 121 is controllable, and especially wherein the control system 300 is configured to control the correlated color temperature of the second device light 121 as a function of time.

Figure 1B:
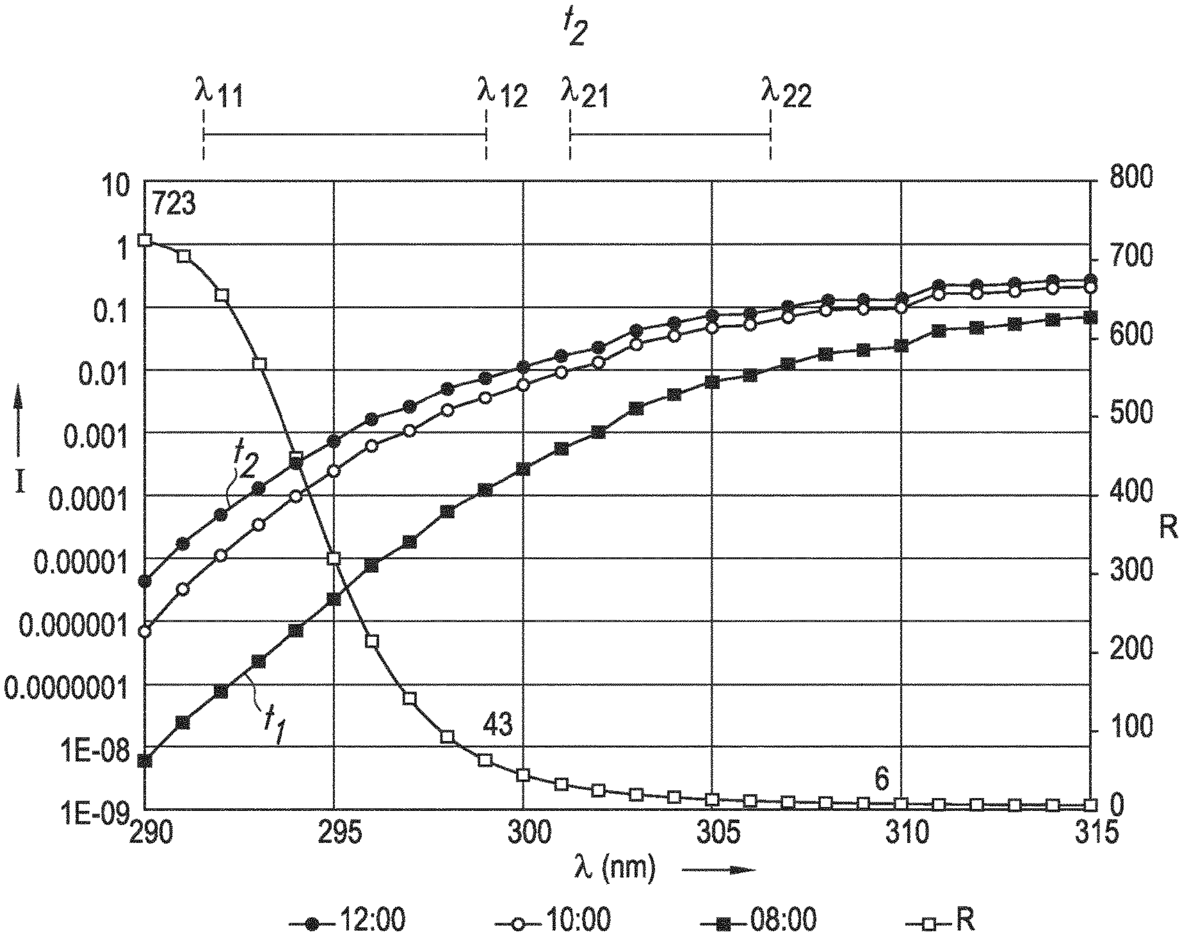
FIG. 1B schematically depicts the natural UVB spectral composition at different times during the day.

FIG. 1B schematically depicts UVB spectral compositions of sunlight at different times during the day (t=12:00, 10:00 or 8:00) in irradiance I in W/m$^2$ versus wavelength $\lambda$ in nm. The ratio change at each wavelength between morning (t=8:00) and afternoon (t=12:00) indicates that the naturally changing spectrum results from more than just an intensity shift. The ratio shift of intensity at afternoon over intensity at morning may be at least 2 orders of magnitude in the shorter wavelength UVB range, such as at around a factor of 723 at 290 nm, while the ratio shift in the total UVB change may only be a factor of 4. For instance, at 300 nm, the ratio shift may be about 43, and at 310 nm the ratio shift may be about 6.

In further embodiments, Ht1 and Ht2 may be radiant fluxes of the higher subrange at time t1 and time t2 respectively, wherein CL is |Lt1−Lt2|/0.5*Lt1+Lt2; CH is Ht1−Ht2|/0.5*Ht1+Ht2; and CL≥2*CH.

FIG. 1B further schematically depicts a selection for the lower subrange and for the higher subrange, as well as for $\lambda_{11}$, $\lambda_{12}$, $\lambda_{21}$ and $\lambda_{22}$. For instance, in the depicted in embodiment, $\lambda_{11}$ may be about 292 nm, $\lambda_{12}$ may be about 299 nm, $\lambda_{21}$ may be about 302 nm, and $\lambda_{22}$ may be about 307 nm.

In further embodiments, $\lambda_{11}$ may be selected from the range of 280-290 nm, $\lambda_{12}$ and $\lambda_{21}$ may be selected from the range of 295-305 nm, and $\lambda_{22}$ may be selected from the range of 310-315 nm.

As described above, the light generating system may be configured to provide system light at a first time t1 and at a second time t2, such as wherein the system light at first time t1 corresponds to sunlight at a high zenith angle and wherein the system light at second time t2 corresponds to system light at a low zenith angle. For instance, as schematically depicted in FIG. 1B, first time t1 may be (about) 8:00, and second time t2 may be (about) 12:00.

In embodiments, first time t1 may be selected from a first day time range, wherein the first day time range is from 04:00 to 10:00 hours, and second time t2 may be selected from a second day time range, wherein the second day time range is from 10:00 to 15:00 hours. In further embodiments, t3 may be selected from a third day time range, wherein the third day time range is from 15:00 to 20:00 hours.

In further embodiments, at the first time t1 the light generating system 1000 may provide first device light 111 having a first radiant flux ratio Rt1 of the radiant flux in the higher subrange relative to the radiant flux in the lower subrange, and at the second time t2 the light generating system 1000 may provide first device light 111 having a second radiant flux ratio Rt2 of the radiant flux in the higher subrange relative to the radiant flux in the lower subrange; especially wherein Rt1/Rt2≥2.

Figure 1C:
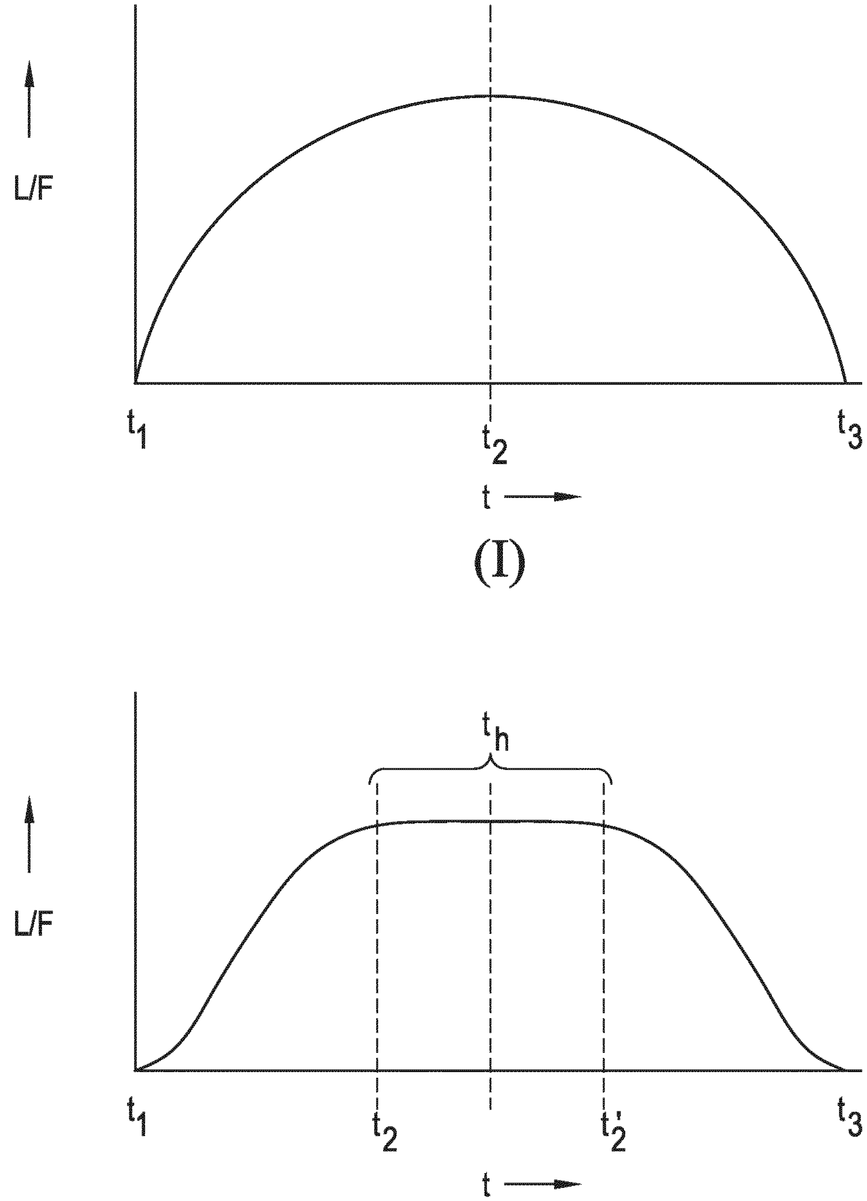
FIG. 1C-D schematically depict aspects related to embodiments of the light generating system.

FIG. 1C schematically depicts aspects of the system light 1001 of two embodiments, referred to as (I) and (II), of the light generating system. Specifically, FIG. 1C schematically depicts the ratio of L/F in the system light 1001 over time t, wherein L is the radiant flux in the lower subrange, and wherein F is the (total) radiant flux in the first wavelength range. For instance, with respect to embodiment (I), the ratio L/F is schematically depicted to increase from t1 to t2, and to decrease from t2 to t3.

In embodiment (II) in FIG. 1C, the ratio L/F is kept essentially constant during a holding period th, wherein the holding period runs from the second time t2, and a second end time t2'. In particular, in the depicted embodiments, during a holding period th a radiant flux Lh of the first device light 111 in the lower subrange $\lambda_{11}$-$\lambda_{12}$ and a radiant flux Hh of the first device light 111 in the higher subrange $\lambda_{21}$-$\lambda_{22}$ are maintained essentially constant, wherein the holding period th is selected from the second day time range. In further embodiments, the holding period th may have a duration of at least 2 h. In further embodiments, the light generating system 1000 may be configured to provide first device with an essentially constant spectral composition during the holding period th.

In further embodiments, Ft1 and Ft2 may be radiant fluxes in the first wavelength range at time t1 and time t2 respectively; Lt1 and Lt2 may be radiant fluxes of the lower subrange at time t1 and time t2 respectively; and Ht1 and Ht2 may be radiant fluxes of the higher subrange at time t1 and time t2 respectively. In further embodiments, Lt2/Ft2≥1.01*Lt1/Ft1, such as Lt2/Ft2≥1.1*Lt1/Ft1, especially Lt2/Ft2≥2*Lt1/Ft1. In further embodiments Ht2/Ft2≤0.99*Ht1/Ft1, such as Ht2/Ft2≤0.98*Ht1/Ft1, especially Ht2/Ft2≤ 0.95*Ht1/Ft1.

Similarly, in embodiments, Ft3 and Lt3 may be radiant fluxes in the first wavelength range and in the lower subrange at time t3 respectively. In further embodiments, Lt2/Ft2>2*Lt3/Ft3. In further embodiments, Ht2/Ft2<0.99*Ht3/Ft3.

In the embodiments depicted in FIG. 1C, the control system 300 may especially be configured to control the first device light 111 such that between t1 and t2 there is a gradual change from Lt1/Ft1 to Lt2/Ft2, and/or especially from Rt1 to Rt2.

Figure 1D:
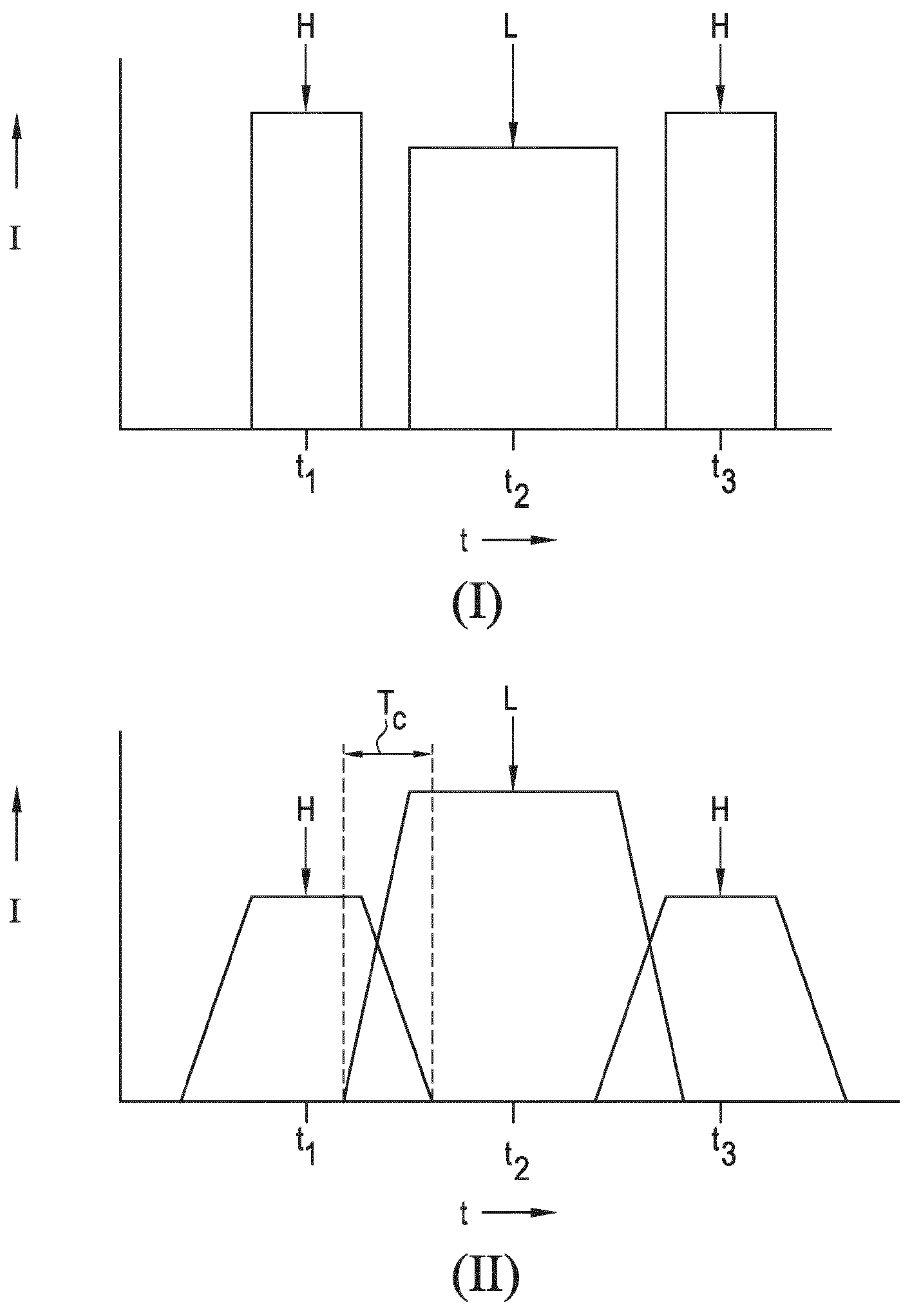

FIG. 1D schematically depicts aspects of the system light 1001 of two embodiments, referred to as (I) and (II), of the light generating system. In particular, FIG. 1D schematically depicts the intensity in the lower subrange L and in the higher subrange H over time t. In the depicted embodiments, the light generating system may be configured at first time t1 (and at third time t3) to provide light in the higher subrange but to provide essentially no light in the lower subrange, whereas at second time t2 the light generating system may be configured to provide light in the lower subrange but to provide essentially no light in the higher subrange.

In particular, in the depicted embodiments: Lt1/Ft1≤0.1; Lt2/Ft2≥0.9; and Lt3/Ft3≤0.1.

In the depicted embodiment, there is a bit of "dead time" wherein essentially no light in the lower subrange and no light in the higher subrange is provided.

In further embodiments, the control system 300 may be configured to control the first device light 111 such that between t1 and t2 there is a stepwise change, especially an instantaneous change from Lt1/Ft1 to Lt2/Ft2. For instance, in such embodiments, t1 may be temporally arranged within 10 s from t2.

In embodiment (II) of FIG. 1D, during a change period tc the time dependent relative change of the wavelength dependent radiant flux of the first device light 111 in the lower subrange may be larger than in the higher subrange.

Figure 2:
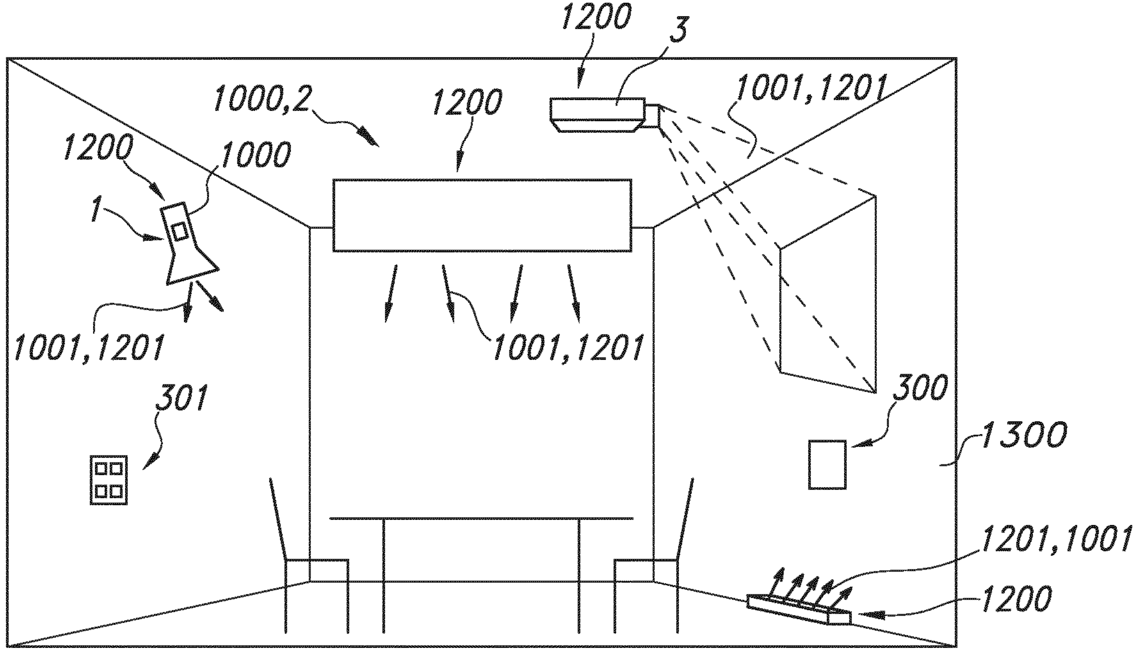
FIG. 2 schematically depicts embodiments of a lighting device. The schematic drawings are not necessarily to scale.

FIG. 2 schematically depicts an embodiment of a luminaire 2 comprising the light generating system 1000 as described above. Reference 301 indicates a user interface which may be functionally coupled with the control system 300 comprised by or functionally coupled to the light generating system 1000. FIG. 2 also schematically depicts an embodiment of lamp 1 comprising the light generating system 1000. Reference 3 indicates a projector device or projector system, which may be used to project images, such as at a wall, which may also comprise the light generating system 1000. Hence, FIG. 2 schematically depicts embodiments of a lighting device 1200 selected from the group of a lamp 1, a luminaire 2, a projector device 3, a disinfection device, a photochemical reactor, and an optical wireless communication device, comprising the light generating system 1000 as described herein. In embodiments, such lighting device may be a lamp 1, a luminaire 2, a projector device 3, a disinfection device, or an optical wireless communication device. Lighting device light escaping from the lighting device 1200 is indicated with reference 1201. Lighting device light 1201 may essentially consist of system light 1001, and may in specific embodiments thus be system light 1001. Reference 1300 refers to a space, such as a room.

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%. The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating system comprising (a) first light generating device and (b) a control system, wherein:

the first light generating device is configured to generate first device light, wherein the first device light comprises light having one or more wavelengths in a first wavelength range of 280-320 nm, wherein the first wavelength range comprises a lower subrange from $\lambda_{11}$ to $\lambda_{12}$ and a higher subrange from $\lambda_{21}$ to $\lambda_{22}$, wherein 280 nm $\leq\lambda_{11}<\lambda_{12}\leq\lambda_{21}<\lambda_{22}\leq$320 nm, and wherein $\lambda_{12}$ and $\lambda_{21}$ are selected from the wavelength range of 290-315 nm, wherein a wavelength dependent radiant flux of the first device light is controllable;

the light generating system is configured to generate system light comprising at least part of the first device light;

the control system is configured to control the wavelength dependent radiant flux of the first device light as a function of time, wherein the light generating system is configured to provide the first device light at a first time t1, at a second time t2, and at a third time t3;

wherein the second time t2 is temporally arranged after the first time t1, and the third time t3 is temporally arranged after the second time t2; and wherein the first time t1, the second time t2, and the third time t3 are temporally arranged in a single day;

wherein relative to a total radiant flux in the first wavelength range the radiant flux of the first device light in the lower subrange is relatively lower at the first time t1 than at the second time t2, and wherein relative to the total radiant flux in the first wavelength range the radiant flux of the first device light in the higher subrange is relatively higher at the first time t1 than at the second time t2; and/or wherein relative to the total radiant flux in the first wavelength range the radiant flux of the first device light in the lower subrange is relatively higher at the second time t2 than at the third time t3, and wherein relative to the total radiant flux in the first wavelength range the radiant flux of the first device light in the higher subrange is relatively lower at the second time t2 than at the third time t3.

2. The light generating system according to claim 1, wherein:

Ft1 and Ft2 are radiant fluxes in the first wavelength range at time t1 and time t2 respectively;

Lt1 and Lt2 are radiant fluxes of the lower subrange at time t1 and time t2 respectively;

Ht1 and Ht2 are radiant fluxes of the higher subrange at time t1 and time t2 respectively; and one or more of the following applies: (a) $Lt2/Ft2\geq1.01*Lt1/Ft1$ and (b) $Ht2/Ft2\leq 0.99*Ht1/Ft1$.

3. The light generating system according to claim 2, wherein one or more of the following applies: (a) $Lt2/Ft2\geq2*Lt1/Ft1$ and (b) $Ht2/Ft2\leq0.95*Ht1/Ft1$.

4. The light generating system according to claim 2, wherein:

Ft3 and Lt3 are radiant fluxes in the first wavelength range and in the lower subrange at time t3 respectively;

$$Lt2/Ft2 > 2*Lt3/Ft3.$$

5. The light generating system according to claim 4, wherein:

$$Lt1/Ft1 \leq 0.1;$$

$$Lt2/Ft2 \geq 0.9.$$

6. The light generating system according to claim 1, wherein t1 is selected from a first day time range, wherein the first day time range is from 04:00 to 10:00 hours, and wherein t2 is selected from a second day time range, wherein the second day time range is from 10:00 to 15:00 hours, and wherein t3 is selected from a third day time range, wherein the third day time range is from 15:00 to 20:00 hours.

7. The light generating system according to claim 1, wherein during a change period $t_c$ a time dependent relative change of the wavelength dependent radiant flux of the first device light in the lower subrange is larger than in the higher subrange.

8. The light generating system according to claim 2, wherein:

$$CL \text{ is } |Lt1 - Lt2|/(0.5*(Lt1 + Lt2))$$

-continued $$CH \text{ is } |Ht1 - Ht2| / (0.5 * (Ht1 + Ht2))$$

$$CL \geq 2 * CH.$$

9. The light generating system according to claim 1, wherein:

at the first time t1 the light generating system provides first device light having a first radiant flux ratio Rt1 of the radiant flux in the higher subrange relative to the radiant flux in the lower subrange;

at the second time t2 the light generating system provides first device light having a second radiant flux ratio Rt2 of the radiant flux in the higher subrange relative to the radiant flux in the lower subrange;

wherein Rt1/Rt2≥2.

10. The light generating system according to claim 1, wherein:

Ft1 and Ft2 are radiant fluxes in the first wavelength range at time t1 and time t2 respectively;

Lt1 and Lt2 are radiant fluxes of the lower subrange at time t1 and time t2 respectively;

wherein the control system is configured to control the first device light such that between t1 and t2 there is a gradual change from Lt1/Ft1 to Lt2/Ft2.

11. The light generating system according to claim 1, wherein:

Ft1 and Ft2 are radiant fluxes in the first wavelength range at time t1 and time t2 respectively;

Lt1 and Lt2 are radiant fluxes of the lower subrange at time t1 and time t2 respectively;

wherein the control system is configured to control the first device light such that between t1 and t2 there is a stepwise change from Lt1/Ft1 to Lt2/Ft2.

12. The light generating system according to claim 3, wherein during a holding period th a radiant flux Lh of the first device light in the lower subrange $\lambda_{11}$-$\lambda_{12}$ and a radiant flux Hh of the first device light in the higher subrange $\lambda_{21}$-$\lambda_{22}$ are maintained essentially constant, wherein the holding period $t_h$ is selected from a second day time range;

the second day time range comprising the range of 9:00 to 16:00 hours.

13. The light generating system according to claim 1, wherein the control system is configured to control the first device light in dependence of a sensor, wherein the sensor comprises a daylight sensor.

14. The light generating system according to claim 1, further comprising a second light generating device, wherein the second light generating device is configured to generate second device light having one or more wavelengths in the visible wavelength range, and wherein in an operational mode of the system the system light comprises one or more of at least part of the first device light and at least part of the second device light.

15. A lighting device selected from the group of a lamp, a luminaire, a phototherapy lighting device, comprising the light generating system according to claim 1.

* * * * *